United States Patent [19]

Lieber et al.

[11] Patent Number: 5,735,816
[45] Date of Patent: Apr. 7, 1998

[54] SPIRAL SHEATH RETAINER FOR AUTOPERFUSION DILATATION CATHETER BALLOON

[75] Inventors: Glen L. Lieber, Poway; Sharon Schwab, San Diego; Don H. Tran, Westminster; Morris H. Deitermann; Jeffrey S. Trinidad, both of San Diego, all of Calif.

[73] Assignee: Medtronic, Inc., Minneapolis, Minn.

[21] Appl. No.: 685,302

[22] Filed: Jul. 23, 1996

[51] Int. Cl.⁶ ................................................. A61M 29/00
[52] U.S. Cl. ............................................ 604/96; 606/194
[58] Field of Search ........................... 604/96–103, 281; 606/192, 194

[56] References Cited

U.S. PATENT DOCUMENTS

| | | | |
|---|---|---|---|
| 3,438,375 | 4/1969 | Ericson | 128/349 |
| 4,195,637 | 4/1980 | Grüntzig et al. | 128/348 |
| 4,637,396 | 1/1987 | Cook | 128/344 |
| 4,706,670 | 11/1987 | Andersen et al. | 128/344 |
| 4,762,130 | 8/1988 | Fogarty et al. | 128/348 |
| 5,226,888 | 7/1993 | Arney | 604/96 |
| 5,295,959 | 3/1994 | Gurbel et al. | 604/96 |
| 5,308,356 | 5/1994 | Blackshear, Jr. et al. | 606/194 |
| 5,484,411 | 1/1996 | Inderbitzen et al. | 604/96 |
| 5,499,995 | 3/1996 | Teirstein | 606/192 |

Primary Examiner—Corrine M. McDermott
Attorney, Agent, or Firm—John R. Duncan; Dianne M. F. Plunkett; Harold R. Patton

[57] ABSTRACT

A spiral balloon perfusion catheter assembly having a retaining wire and method of making the balloon. Also, a retaining wire for such a catheter and method of forming the retaining wire. A typical spiral catheter balloon has a spiral configuration of lobes and channels mounted on a catheter extending beyond the balloon ends. A retaining wire formed from a shape memory alloy is configured to have a central region having a spaced spiral configuration conforming to the spiral balloon channel and end regions configured to have a contiguous spiral configuration conforming to the catheter diameter. When placed over a spiral balloon, the central spiral region prevents expansion of the channel when the balloon is inflated, while the end regions secure the retaining wire to the catheter. Preferred shape memory alloys comprise nickel and titanium. The retaining wire is made by heating the wire above the crystal phase change temperature of the alloy, shaping the spirals then cooling the product below the crystal phase change temperature. The spiral end regions may be unwound and placed over the catheter adjacent to the balloon with the wire in the central spiral region conforming to the balloon channel.

10 Claims, 1 Drawing Sheet

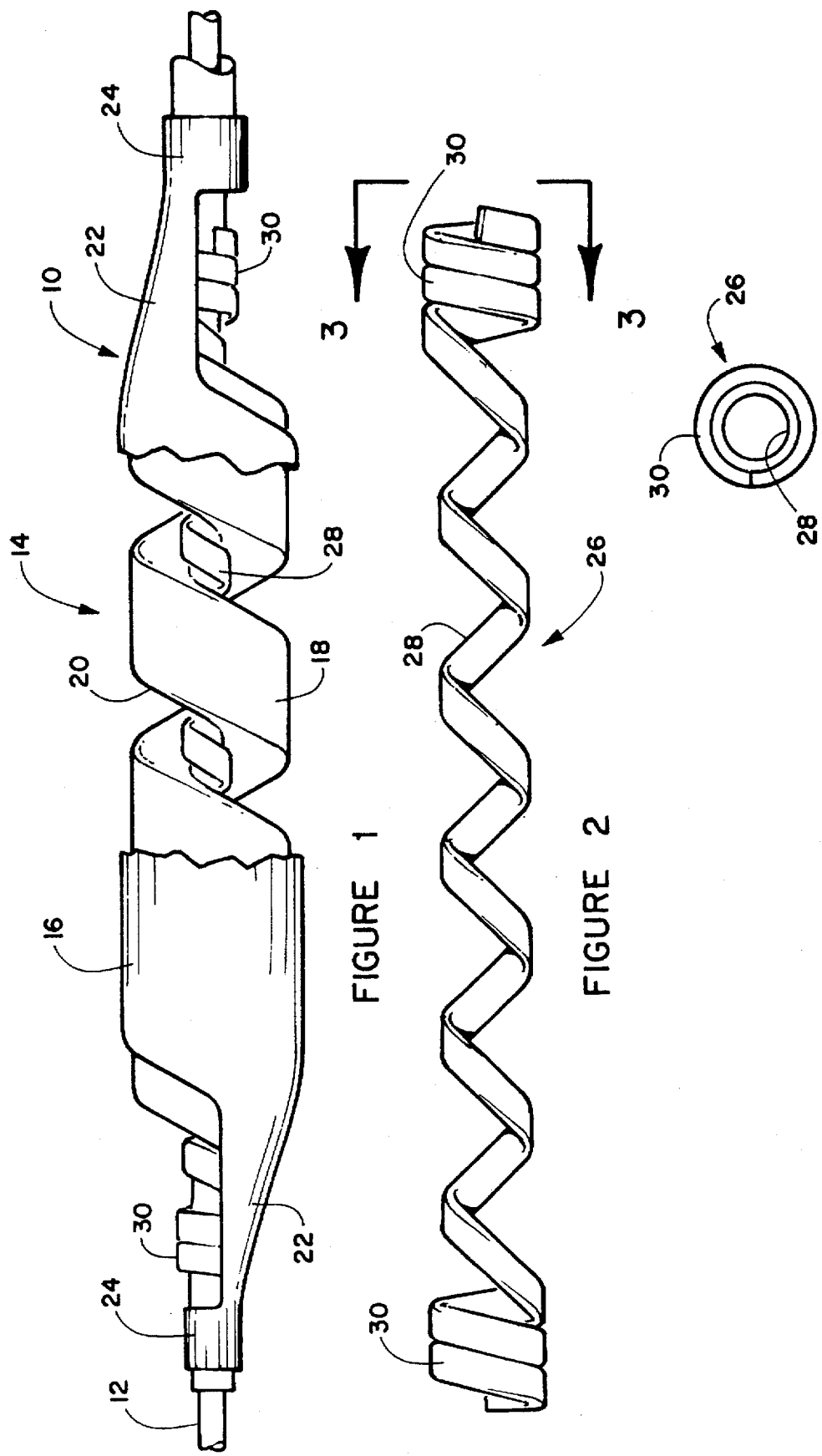

SPIRAL SHEATH RETAINER FOR AUTOPERFUSION DILATATION CATHETER BALLOON

BACKGROUND OF THE INVENTION

This invention relates to methods and apparatus for improving the performance of autoperfusion dilatation catheters as used in angioplasty and the like, and more specifically to an arrangement for maintaining a spiral sheath configuration during those procedures.

Dilatation balloon catheters are well known and used regularly for coronary angioplasty procedures and other similar procedures. Atheromatous plaque adhering to a blood vessel wall and restricting blood flow therethrough is compressed against the vessel wall by a balloon that is positioned in the vessel at the plaque location. This dilates the vessel lumen to permit increased blood flow.

A typical balloon catheter includes two lengthwise lumens or channels, one for inflation of an inflatable balloon sealed to the distal catheter end and the other for insertion of a guidewire extending though the catheter to aid in positioning the catheter during use.

Many catheters have been designed for particular uses, having a variety of configurations, methods of construction and methods of use. Most have a generally tubular balloon that, when inflated, temporarily cuts off blood flow through the vessel. Serious consequences can occur when blood flow is stopped for an extended period. Therefore, inflation duration is generally relatively short, typically no more than 150–180 seconds. Longer inflation periods would be very desirable, since better plaque compression could be accomplished. Also, some patients cannot tolerate even short time blood occlusion in some vessels.

Attempts have been made to develop balloon configurations that will permit at least some continued blood flow during plaque compression. For example, catheters having an additional lumen have been used, with openings between the catheter exterior and the added lumen at both ends of the balloon, so that limited blood flow can bypass the balloon occlusion. However, this arrangement has had limited success, since only a very limited amount of blood can flow though the lumen and adding the lumen increases the diameter of the catheter, which itself will tend to retard blood flow. Thus, at most this arrangement will allow a very slightly longer balloon inflation period.

Fogarty et al. in U.S. Pat. No. 4,762,130, Blackshear et al. in U.S. Pat. No. 5,308,356 and others have disclosed catheter balloons with a spiral or corkscrew-like configuration when expanded. Such perfusion balloon catheters are intended to allow blood to flow in a spiral channel path past the balloon during balloon inflation. However, in practice, little if any blood flow is found to occur with these spiral balloons, apparently due to blockage of the balloon channels by the arterial intima or lining and/or expansion of the balloon in the channel region decreasing channel cross sectional area.

Attempts have been made to reinforce the channel of a spiral catheter balloon with a spiral metal or plastic wire engaging the balloon spiral channel, as described by Gurbel et al. in U.S. Pat. No. 5,295,959 and Inderbitzen et al. in U.S. Pat. No. 5,484,411.

These reinforcing wires have been less than fully successful, primarily because expansion of the balloon tends to stress the wire to the point where the channel shape is not retained and the wire is stretched beyond its elastic limits. Further, the wire may be excessively bent while negotiating tortuous paths while the balloon catheter is being emplaced. Where the wire has been stressed to the point where the modulus of elasticity is exceeded the balloon cannot be returned to its original diameter during rewrapping, making the balloon difficult and dangerous to withdraw. In addition, where the wire is simply bonded to the balloon or wrapped around the catheter adjacent to the balloon ends, the bond may be released or the end wraps may unwrap, when the balloon is expanded, resulting in a loose or partially loose wire, which can be very difficult to remove from a body lumen.

Thus, there is a continuing need for improved spiral catheter balloons including a spiral channel retainer that will maintain sufficient perfusion capacity while the balloon is inflated, that will maintain the channel shape during inflation, that will not become permanently deformed during catheter movement through a tortuous lumen path, that will return fully to the uninflated diameter and shape when deflated and that will remain securely attached to the catheter during balloon emplacement, inflation, deflation and withdrawal.

SUMMARY OF THE INVENTION

The above-noted problems, and others, are overcome in accordance with this invention by spiral balloon perfusion catheter assembly that basically comprises a catheter having a balloon configured in an exterior spiral lobe and channel pattern and a wire retainer secured to the catheter and having a spiral region lying along the balloon channels to retain the channel shape during balloon inflation. The wire retainer is formed from a shape memory alloy, preferably a alloy having selected proportions of nickel and titanium.

The wire retainer has a center region with a spaced spiral conforming to the balloon channel. Preferably the spiral is cylindrical in over all configuration, with a straight axis. End regions are configured as cylindrical contiguous spirals, with the inside diameter of the cylindrical spiral conforming to the exterior diameter of the catheter adjacent to the balloon. Preferably, the wire is configured with a basically rectangular, flat, cross section with the wire width generally parallel to the spiral axis. A round wire, typically having a diameter of from about 0.002 to 0.006 inch or a narrow flat wire may be used. Preferably, the wire is flat with a width of from about 0.02 to 0.03 inch and a thickness of from about 0.002 to 0.005 inch. Wire edges are preferably rounded.

The wire retainer is preferably made by heating the wire above the crystal phase change temperature, to the Austenite state, and shaping the wire to the desired spiral configuration in the central and end regions, typically by wrapping on a suitable cylindrical mandrel. The sections for the different regions may have the same or different diameters and pitches to produce corresponding cylindrical spirals. Once shaping is complete, the wire is cooled to a temperature below the crystal phase change temperature, to the Martensite state. A nickel-titanium alloy having a crystal phase change temperature well above room temperature is preferred. The resulting product can be severely flexed, such as by unwinding an end spiral and fitting it over a catheter, without permanent deformation. In addition the wire retainer is highly resistant to deformation, to resist expansion in the central region during balloon inflation, so that the channels are kept substantially open.

Once the wire retainer is mounted on the balloon and catheter, the end region contiguous spirals are preferably encapsulated. Any suitable encapsulation may be used, such as impregnation with an adhesive such as a UV curing adhesive, a cyanoacrylate or an epoxy, enclosure in a heat shrink tube or covering with tape. For convenience and effectiveness, adhesives are preferred.

It is, therefore, an object of this invention to provide a spiral balloon perfusion catheter assembly which provides improved perfusion during dilation. Another object is to provide a retaining wire for spiral balloons that when emplaced on such a balloon will maintain a substantially constant channel configuration during balloon inflation. A further object is to provide a retaining wire for spiral balloons that will resist permanent deformation during balloon catheter insertion into a body lumen and during balloon inflation. Yet another object is to provide a retaining wire that is more securely attached to a catheter adjacent to a balloon. A further object is to provide a convenient and rapid method of making a spiral balloon perfusion catheter assembly having improved perfusion performance. Still another object is to provide convenient and rapid methods of making an improved spiral balloon channel retaining wire.

BRIEF DESCRIPTION OF THE DRAWING

Details of the invention, and of preferred embodiments thereof, will be further understood upon reference to the drawing, wherein:

FIG. 1 is a side elevation view, partly cut away, of a spiral balloon perfusion catheter assembly of this invention;

FIG. 2 is a side elevation view of a wire retainer for use in a spiral balloon perfusion catheter assembly; and FIG. 3 is a section view taken on line 3—3 in FIG. 2.

DETAILED DESCRIPTION OF PREFERRED EMBODIMENTS

Referring to FIG. 1, there is seen a spiral balloon perfusion catheter assembly 10, including a conventional catheter 12, an inflatable spiral balloon 14 and a sheath 16 over balloon 14.

Any suitable catheter 12 may be used. Typically, catheter 10 may include a polymer tube incorporating a body spring and having one or more lumens for passage of a guidewire, a channel for a fluid to inflate the balloon, etc.

Balloon 14 is wrapped to provide a small cross section for insertion in a body lumen. When positioned at a desired location, balloon 14 is inflated to assume the configuration shown in FIG. 1. The spiral configuration of lobes 18 and channels 20 permits perfusion of blood past the balloon, permitting inflation for longer periods without excessively slowing blood flow.

A sheath 16 is preferably provided over balloon 14 and bonded thereto to prevent arterial intima from entering and at least partially blocking channels 20. Sheath 16 includes ribs 22 extending from the ends of the balloon-engaging sheath portion and collars 24 for securing the ends of ribs 22 to catheter 12.

A wire retainer 26 is provided to maintain channels 20 at the proper depth and prevent expansion of those channels during balloon inflation, with the corresponding reduction in perfusion path cross section. Wire retainer 26 has a spaced spiral center region 28 conforming in shape to channels 20 and radially wound contiguous end regions 30 configured to provide an interference fit over catheter 12 adjacent to the ends of balloon 14. The inside diameters of end regions 30 may be the same or different, depending upon the outside diameters of catheter 12 at the ends of balloon 14.

In order to fully resist expansion forces during inflation of balloon 14 while permitting easy assembly of the balloon and wire retainer 26, the wire retainer is formed from a shape memory alloy. Any suitable shape memory alloy may be used. Typically, suitable alloys primarily comprise nickel and titanium. Typical preferred proportions are about 55.7 wt % nickel and about 43.9 wt % titanium and trace amounts of other elements, e.g. chromium, carbon, oxygen, hydrogen. Such alloys are commercially available from Dynaloy, Inc., Shape Memory Applications, Inc. and others.

In order to constrain the bottoms of channels 20 in an optimum manner, the wire retainer 26 preferably has a generally rectangular to oval cross section, with the longer side lying generally parallel to the balloon axis. Widths of from about 0.02 to 0.03 inch and thicknesses of from about 0.002 to 0.005 inch are generally optimum. The edges of the wire retainer are preferably rounded by any suitable method, such as chemical etching. If desired, the wire retainer may be bonded to the bottom of channel 20 such as by an adhesive, heat sealing or the like.

Along channels 20, wire retainer 26 has a central region with a cylindrical spiral configuration matching that of the channels. At the ends of the central region, wire retainer 26 transitions to a contiguous radially wound form corresponding to catheter diameter in end regions. For best results, the wire retainer in the end regions 30 is wrapped to form from about 1.5 to 3 coils. Optimally, about 2.5 end region turns are provided at the proximal end of balloon 14 and about 2 turns at the distal end with the wire dimensions described above. With relatively small cross section wire, the number of coils may be increased to up to 6 to 10 coils.

In order to positively prevent any unraveling of the wire retainer 26 end region coils 30 during full inflation of balloon 14, those coils are preferably encapsulated. The encapsulation of end region coils 30 reinforce the retention of the wire retainer on the catheter when balloon 14 is inflated to high pressure and creates a more uniform, smooth, surface to aid insertion and removal of the catheter. Typically, an adhesive such as an epoxy or cyanoacrylate, a heat shrinkable sleeve, tape, etc., could be used. Of these, Loctite® (manufactured by Loctite Corp. in Hartford Conn.) #406 is preferred because of its high tensile and peel strength and rapid cure.

The wire retainer is made by wrapping the shape memory alloy wire onto an appropriately configured mandrel while heating the wire above the transition temperature. The mandrel has diameters over selected lengths corresponding to the spiral central region 28 and each radial end region 30. Typically, an end of the wire may be inserted into a hole in the mandrel and the opposite end grasped in pliers. While heating, the wire is wrapped in the desired pattern around the mandrel, then cooled below the transition temperature. After the mandrel is cooled, excess wire is trimmed away and the wire retainer 26 is carefully unwound from the mandrel. Wire retainer 26 is then installed on a balloon 14 by wrapping the center region 28 and fitting it into channels 20. Each end region 30 is then unrolled and rerolled over catheter 12 adjacent to balloon 14. The end region coils are then encapsulated, if desired, and sheath 16 is installed.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

We claim:

1. A spiral balloon perfusion catheter assembly, which comprises:

a catheter;

a catheter balloon mounted on a distal end of said catheter substantially coaxial with said catheter;

said catheter balloon having an exterior spiral lobe and channel pattern; and a wire retainer having a central spiral region conforming to said channel and radially wound end regions wrapped around said catheter adjacent to primal and distal ends of said catheter balloon;

said wire retainer formed from a shape memory alloy that resists permanent deformation when exposed to balloon expansion pressures.

2. The assembly according to claim 1 wherein said shape memory alloy is formed from a composition consisting essentially of nickel and titanium.

3. The assembly according to claim 2 wherein said alloy comprises about 55.7 wt % nickel and about 43.9 wt % titanium.

4. The assembly according to claim 1 wherein said wire retainer has a cross section of approximately rectangular to oval shape, with a width of from about 0.02 to 0.03 inch and a center thickness of from about 0.002 to 0.005 inch, with said width lying generally parallel to said balloon axis.

5. The assembly according to claim 4 wherein edges of said wire retainer are rounded.

6. The assembly according to claim 1 said radially wound end regions are wound in a contiguous relationship with from about 1.5 to 10 circumferential coils and said radially wound end regions are encapsulated.

7. The assembly according to claim 6 wherein said radially wound end regions are encapsulated with a material selected from the group consisting of an adhesive, a heat-shrink plastic sleeve, tape and combinations thereof.

8. A retainer for a spiral balloon perfusion catheter assembly, which comprises:

a wire retainer formed from a shape memory alloy that resists permanent deformation when exposed to balloon expansion pressures, said shape memory alloy consisting essentially of nickel and titanium;

said wire retainer having a cross section of approximately rectangular shape with rounded corners, and having a width of from about 0.02 to 0.03 inch and a center thickness of from about 0.002 to 0.005 inch, with said width lying generally parallel to said straight axis;

said wire retainer formed as a cylindrical spiral around a substantially straight axis;

said wire retainer having a central region configured as a spiral with said spiral axially spaced;

end regions at each end of said wire retainer configured as a spiral with said spiral contiguous;

said end regions each including from about 1.5 to 10 circumferential coils; and said end regions being bonded together with a cyanoacrylate adhesive.

9. The retainer according to claim 8 wherein said alloy is about 55.7 wt % nickel and about 43.9 wt % titanium.

10. The retainer according to claim 8 wherein said end regions have from about 1.5 to 3 circumferential coils.

* * * * *